US 6,618,127 B2

(12) United States Patent
Yang et al.

(10) Patent No.: US 6,618,127 B2
(45) Date of Patent: Sep. 9, 2003

(54) SPRAY PLUME CHARACTERIZATION SYSTEM

(75) Inventors: Steve Y. T. Yang, Mississauga (CA); Anthony Y. Qu, Mississauga (CA); Shabbir Anik, Mississauga (CA)

(73) Assignee: Patheon Inc., Mississauga (CA)

( * ) Notice: Subject to any disclaimer, the term of this patent is extended or adjusted under 35 U.S.C. 154(b) by 0 days.

(21) Appl. No.: 09/991,684

(22) Filed: Nov. 26, 2001

(65) Prior Publication Data

US 2003/0098968 A1 May 29, 2003

(51) Int. Cl.$^7$ ................................................ G01P 3/36
(52) U.S. Cl. ....................................................... 356/27
(58) Field of Search ........................... 356/27, 336, 339

(56) References Cited

U.S. PATENT DOCUMENTS

| | | | |
|---|---|---|---|
| 4,136,950 A | * | 1/1979 | Labrum et al. ................ 356/28 |
| 4,628,465 A | | 12/1986 | Ito et al. ...................... 364/521 |
| 5,396,333 A | * | 3/1995 | Aleshin et al. ............... 356/601 |
| 5,701,156 A | * | 12/1997 | Pierce ........................... 356/23 |
| 6,404,494 B1 | * | 6/2002 | Masonis et al. .............. 356/338 |

FOREIGN PATENT DOCUMENTS

| | | |
|---|---|---|
| DE | 199 04 319 A1 | 8/2000 |
| WO | WO 01/13092 A1 | 2/2001 |

* cited by examiner

*Primary Examiner*—F. L. Evans
*Assistant Examiner*—Kara Geisel

(57) ABSTRACT

The density of a spray plume generated by an aerosol delivery system ("ADS") may be characterised by illuminating a face of the plume with light and then imaging the plume. The shape of the plume may be characterised by operating the ADS in a controlled manner to form a first spray plume. A face of the plume is illuminated and the plume imaged from a first side parallel to the spray axis of the plume. The ADS is then again operated in the controlled manner to form a second spray plume. A face of the second plume is illuminated and the second plume imaged from a second side which is parallel to the spray axis of the plume and perpendicular to the first side.

18 Claims, 2 Drawing Sheets

SPRAY PLUME CHARACTERIZATION SYSTEM

BACKGROUND OF THE INVENTION

The present invention relates to systems for and methods of characterizing aerosol spray plumes, more particularly, to systems and methods that illuminate an aerosol spray plume and utilize optical techniques to characterize the plume.

A pulmonary delivery route is preferred for medicines used in the treatment of many pulmonary diseases and respiratory ailments because the dose of medication can be delivered to tissues that can more efficiently absorb the medication, thereby more readily bringing relief to patients. In addition, medications for non-respiratory problems such as flu vaccines, insulin and migraine relievers can also be delivered with an aerosol delivery system (ADS). However, patients with different medical conditions present challenges respecting the safety and efficacy of the aerosol delivery system, in part due to the different physical properties of the different formulations for different medications. The fluid dynamic characterization of the aerosol spray of a particular medicine emitted by a metered nasal spray device is therefore crucial in determining the overall performance of the inhaler as a drug delivery device.

Spray plume characterization is an integral part of the regulatory submissions necessary for Food and Drug Administration approval. The plume acts as a quick and precise indication of the overall performance of most ADS. Most importantly, drug targeting can be optimized by the appropriate choice of aerosol delivery system and formulation. Further, studies of characteristics of spray plumes from different ADSs can be used to guide product design.

One approach to spray plume characterisation is described in WO 01/13092 of Image Therm Engineering published Feb. 22, 2001. In the described system, a laser generates a fan-shaped sheet of light which is aligned with, and passes through, the spray axis of a spray plume in order to illuminate a slice of the plume along the spray axis. A digital camera positioned to a side of the plume captures consecutive images of the slice.

The laser is then adjusted to generate a fan-shaped sheet of light which is transverse to the spray axis in order to illuminate a transverse cross-sectional slice of a spray plume. The digital camera is re-positioned to a position above the plume to capture consecutive images of the transverse plume slice.

While this system provides characteristics of the plume, the plume is not fully characterised and it would be advantageous to have a system which provided fuller information on the characteristics of the plume.

SUMMARY OF THE INVENTION

The density of a spray plume generated by an aerosol delivery system ("ADS") may be characterised by illuminating a face of the plume with light and then imaging the plume. The shape of the plume may be characterised by operating the ADS in a controlled manner to form a first spray plume. A face of the plume is illuminated and the plume imaged from a first side parallel to the spray axis of the plume. The ADS is then again operated in the controlled manner to form a second spray plume. A face of the second plume is illuminated and the second plume imaged from a second side which is parallel to the spray axis of the plume and perpendicular to the first side.

According to the present invention, there is provided a method of characterising a spray plume, comprising: illuminating a spray plume with light such that said light impinges upon the entirety of a first side of said spray plume; imaging said illuminated spray plume from a second side perpendicular to said first side.

According to another aspect of the invention, there is provide a method of characterising a spray plume, comprising: operating an aerosol delivery system in a controlled manner to form a first spray plume; illuminating said first spray plume with light such that said light impinges upon the entirety of a face of said first spray plume; imaging said first spray plume from a first side parallel to a spray axis of said spray plume; operating said aerosol delivery system in said controlled manner to form a second spray plume; illuminating said second spray plume with light such that said light impinges upon the entirety of a face of said second spray plume; imaging said second spray plume from a second side parallel to a spray axis of said spray plume, said second side being perpendicular to said first side.

According to a further aspect of the invention, there is provided a system for spray plume characterisation, comprising: a source of non-coherent illumination positioned for illuminating a spray plume with light such that said light impinges upon the entirety of a first side of said spray plume; an imaging device camera for imaging said illuminated spray plume from a second side perpendicular to said first side.

According to another aspect of the invention, there is provided a system of characterising a spray plume, comprising: an actuator for operating an aerosol delivery system in a controlled manner to form a spray plume; a source of illumination for illuminating said spray plume with light such that said light impinges upon the entirety of a face of said spray plume; an imaging device positioned for imaging said spray plume from a side parallel to a spray axis of said spray plume; a turntable having a rotational axis parallel to said spray axis for rotating said aerosol delivery system.

According to a further aspect of the invention, there is provided a system of characterising a spray plume, comprising: means for operating an aerosol delivery system in a controlled manner to form a first spray plume and, subsequently, a second spray plume; means for illuminating said first spray plume with light such that said light impinges upon the entirety of a face of said first spray plume and for illuminating said second spray plume with light such that said light impinges upon the entirety of a face of said second spray plume; and means for imaging said first spray plume from a first side parallel to a spray axis of said spray plume and for imaging said second spray plume from a second side parallel to a spray axis of said spray plume, said second side being perpendicular to said first side.

BRIEF DESCRIPTION OF THE DRAWINGS

In the figures which illustrate example embodiments, FIG. 1 is a perspective view of a system made in accordance with this invention, FIGS. 2 and 3 are schematic plan views of the system of FIG. 1 which illustrate an aspect of the operation of the system.

DETAILED DESCRIPTION

The spray characterization system of the present invention is capable of providing images of the time-evolution, particle distribution, divergence angle, and intrinsic plume pattern of aerosol sprays. The spray data characterization system is a non-intrusive system that may be adjustable and is capable of capturing and displaying information representative of the time evolution of an aerosol spray for substantially complete geometrical imaging analysis. The modular hardware of the system allows easy customization to meet needs of a variety of spray testing applications.

Figure 1:
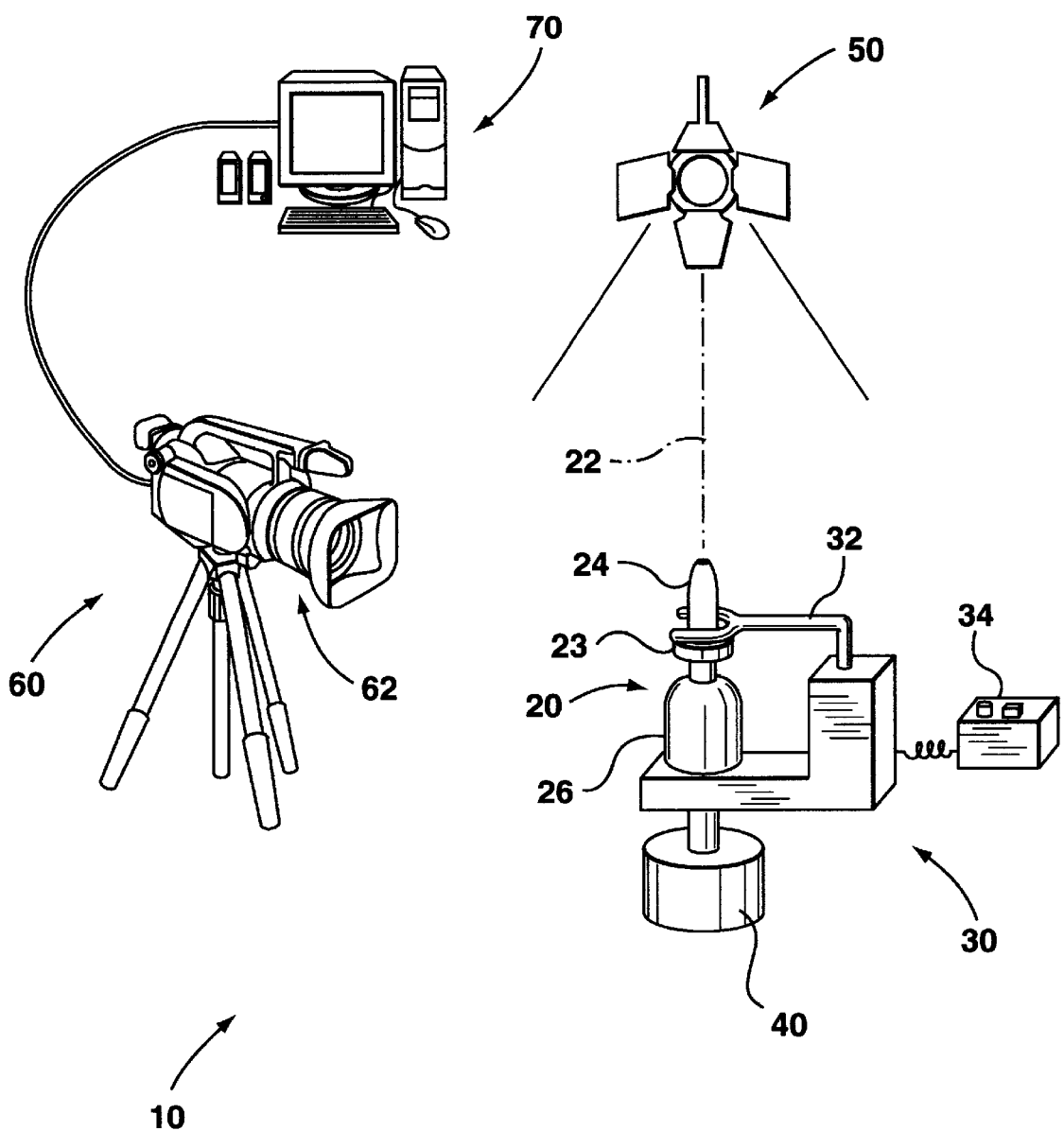

FIG. 1 show a spray data characterization system 10 that generates data representative of the characteristics of a spray plume as emitted from a spray pump 20. The system 10 includes a spray pump actuator 30, turntable 40, illumination device 50 and imaging device 60 connected to a processor 70. As is typical, the spray pump 20 is designed to dispense a metered amount of medicament when a collar 22 on its nozzle 24 is compressed toward reservoir 26.

The actuator 30 of system 10 has a reciprocating actuator arm 32 with an end overlying collar 22. The actuator is designed to position the spray pump 20 so as to direct an aerosol spray dispensed from pump 20 along a spray axis 22. The arm 32 reciprocates in a controlled fashion, with a selectable force and stroke, when suitably prompted by actuator control unit 34. Actuator 30 may be an electro-mechanical transducer that converts electrical control signals from control unit 34. In this regard, a suitable actuator is the Nasal Spray Pump Actuator sold by InnovaSystems of Pennsauken, N.J. The InnovaSystems actuator includes built-in programmability to control key parameters involved with aerosol spray pumping, such as pumping force and duration. In alternative embodiments, hydraulic, pneumatic, or mechanical linkage actuators may be substituted.

The illumination device 50 is arranged to continuously illuminate any spray plume generated by spray pump 20. Device 50 may emit a continuous strong conical beam of non-coherent light that is directed so as to illuminate the entire plume. The beam of the illumination device 50 may be centered with respect to the spray axis 22 so that the plume is more evenly illuminated. It has been found to be suitable to illuminate the plume to a brightness of 300 Watts. The illumination device may employ a halogen light bulb as the light source, such as Kaiser 300 W probe light.

The imaging device 60 has an imaging lens system 62 which may provide zoom (magnification) capabilities. Device 60 outputs images to computer 70. Ideally, the imaging device 60 is capable of an imaging acquisition speed (i.e., framing rate) and spatial resolution sufficient to accurately capture the time evolution of a spray plume. For example, the imaging device 60 may provide a framing rate in the neighbourhood of sixty frames per second (fps) at a resolution of 720×480 pixels and thirty-two bit intensity. Device 60 may comprise three charge coupled devices ("CCD"s) to provide colour images. Suitably, the imaging device may be a digital camcorder such as a Canon GL 1 digital camcorder.

The processor 70 may be a general-purpose computer, such as a PC-type computer or a work station, operating under software control. For example, the computer may be an Intel Pentium-based computer system running a Windows ME operating system. The computer has suitable I/O devices such as a keyboard, mouse, and display.

Figure 2:
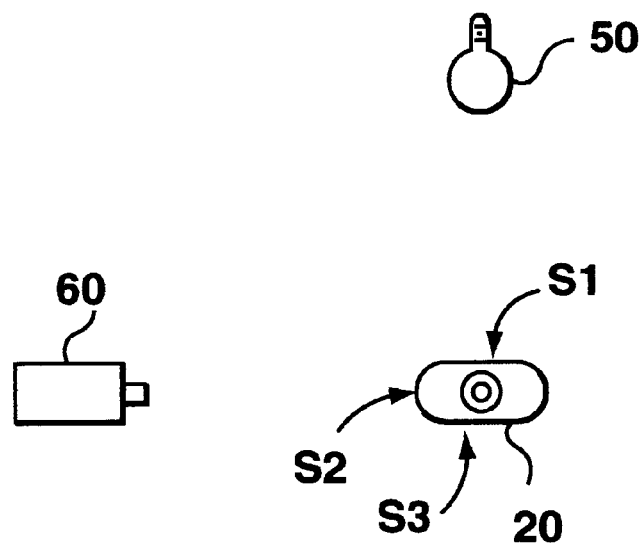

Optionally, the illumination device 50, imaging device 60 and turntable 40 may be mounted to a common platform at fixed relative positions to each other. This fixed positioning is such that, as seen in FIG. 2, light from the illumination device 50 impinges at a first side S1 of spray pump 20 and imaging device 60 takes images from a second side S2 of the spray pump, with side S2 being perpendicular to side S1.

A calibration operation is performed once, where the components are mounted to a common platform, or before each operation where the components are not in fixed relative positions. The calibration operation involves placing a target of known dimensions at the spray axis and then imaging this with the imaging device 60 in order to provide scale information to processor 70.

In operation, activator control unit 34 may be programmed for a stipulated activation force and duration which is considered appropriate for the particular spray pump 20 and formulation under test. This force and duration information is passed to processor 70 (either electronically or manually) for recordal. The pump 20, filled with the formulation under test, is loaded into the actuator 30. The illumination device 50 is turned on. The imaging device 60 is activated, set to capture images at a suitable frame rate, and focussed on a field of view including the tip of the nozzle 24. These sequential images are passed to processor 70 for recordal.

Figure 3:
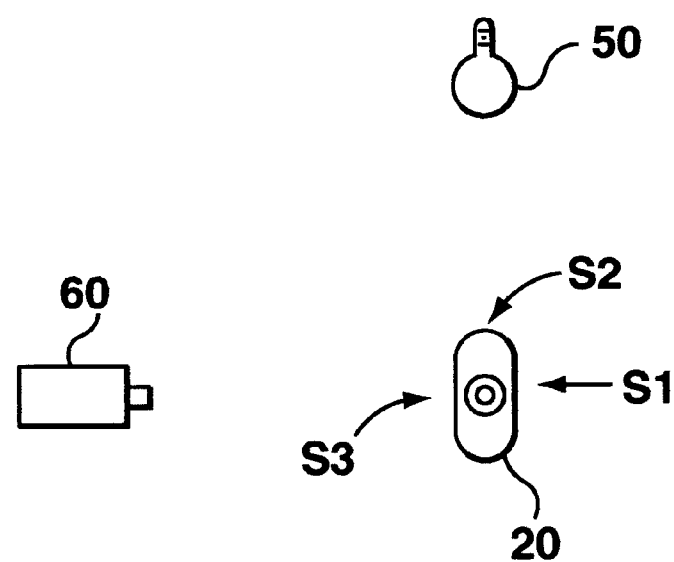

An activation signal is then given to the actuator via the actuator controller 34 such that arm 32 reciprocates to actuate pump 20 to spray formulation. The resulting time-evolving spray plume is captured by the imaging device 60 and recorded by processor 70. In this regard, it will be noted that because light from the illumination device impinges upon the entirety of side S1 of the spray plume, the entire plume is illuminated. In consequence, the image of the plume imaged by imaging device 60 is an image of the complete plume, collapsed into two-dimensions. Thus, the image will indicate the density of the plume. Recording of the spray plume may continue as long as desired in order to fully characterise the time-evolution of the plume. Once this recording is complete, turntable 40 is used to rotate actuator 30, and hence spray pump 20, through ninety degrees. This re-orients the spray pump from its position shown in FIG. 2 whereat side S2 of the pump faces imaging device 60 to its position shown in FIG. 3 whereat side S3 of the pump faces the imaging device 60. (As will be apparent, side S3 of the pump is perpendicular to side S2 of the pump.) Another activation signal is then given to the actuator 30 via the actuator controller 34. This results in a second time-evolving spray plume which is generated with the same force and duration parameters as was the first spray plume. The second plume is captured by the imaging device 60 and recorded by the processor 70. Again, recording may continue as long as desired.

The first and second plumes may be assumed to be identical in view of the fact that they are generated with the same parameters. Consequently, a given image of the first plume may be paired with a time-equivalent image of the second plume to provide two images of, effectively, the same plume from different angles. Since these two two-dimensional images are taken from two different sides, which sides are at ninety degrees to one another, these two-images completely characterise the three-dimensional shape of these identical plumes. Processor 70 may be used to provide time-equivalent image pairings for this purpose.

Any zoom feature of the lens system 62 of the imaging device 60 may be used to quantify partial characteristics of spray plumes emitted from spray pump 20. For example, precise plume angles, defined within the boundaries of travelling spray particles, can be analysed along with associated characteristics such as plume intensity and plume orientation. Optionally, and as illustrated for the illumination device 50 of FIG. 1, the beam of the illumination device may be adjustable in its extent. By cutting off a portion of the beam, only a portion of the spray plume may be illuminated as an alternative technique for use in quantifying partial characteristics of spray plumes emitted from the spray pump.

The system 10 may also be used to quantity plume characteristics from full spray plume images. From inception to dissipation, full spray plume images manifest details of time evolving spray plume formation that can be sequentially visualized. Each image is representative of a characteristic pattern of the full spray plume in development at a specific time frame. Each image discloses intrinsic plume characteristics on plume intensity, two-dimensional plume profile, shape of the aerosol front and plume dissipation.

System 10 may also be used to quantify spray speed. For example, the position of the travelling plume front moving along the spray axis 22 may be noted from images taken at two different times. The difference in the position of the front along the spray axis divided by the time difference yields an indication of spray speed. Obviously, a vertically projected spray slows with time due to gravity, thus, the images chosen for measurement of spray speed are best chosen near the time of inception of the plume.

Turntable 40 may be rotated manually or by a suitable activation signal, optionally from processor 70.

While the system 10 has been described in conjunction with a spray pump as the ADS, obviously system 10 may be modified for use with any ADS.

The invention may be embodied in other specific forms without departing from the spirit or essential characteristics thereof. The present embodiments are to be considered in respects as illustrative and not restrictive, the scope of the invention being indicated by the appended claims rather than by the foregoing description, and all changes which come within the meaning and range of the equivalency of the claims are therefore intended to be embraced therein.

What is claimed is:

1. A method of characterising a spray plume, comprising:
   illuminating a spray plume with light such that said light impinges upon the entirety of a first side of said spray plume;
   imaging said illuminated spray plume from a second side perpendicular to said first side.

2. The method of claim 1 wherein each of said first side and said second side is parallel to a spray axis of said spray plume.

3. The method of claim 2 wherein said light is non-coherent.

4. The method of claim 1 wherein said imaging captures at least two images of said illuminated spray plume separated in time by a known interval and further comprising determining a speed of said spray plume from said at least two images and said known interval.

5. The method of claim 2 wherein said imaging is colour imaging.

6. A method of characterising a spray plume, comprising:
   operating an aerosol delivery system in a controlled manner to form a first spray plume;
   illuminating said first spray plume with light such that said light impinges upon the entirety of a face of said first spray plume;
   imaging said first spray plume from a first side parallel to a spray axis of said spray plume;
   operating said aerosol delivery system in said controlled manner to form a second spray plume;
   illuminating said second spray plume with light such that said light impinges upon the entirety of a face of said second spray plume;
   imaging said second spray plume from a second side parallel to a spray axis of said spray plume, said second side being perpendicular to said first side.

7. The method of claim 6 wherein said light is non-coherent.

8. The method of claim 6 wherein said imaging said first spray plume captures at least two images of said first spray plume.

9. The method of claim 8 wherein said at least two images are separated in time by a known interval and further comprising determining a speed of said spray plume from said at least two images and said known interval.

10. The method of claim 8 wherein one of said images is a magnified image of a portion of said first spray plume at an outer boundary of said first spray plume.

11. The method of claim 8 wherein said imaging said second spray plume captures at least two images of said second spray plume and further comprising matching an image of said first spray plume with a time-equivalent image of said second spray plume.

12. The method of claim 6 wherein each said imaging is colour imaging.

13. The method of claim 6 wherein said illuminating a first spray plume illuminates a side of said spray plume.

14. The method of claim 6 wherein said illuminating a first spray plume illuminates a side of said spray plume perpendicular to said first side.

15. The method of claim 14 wherein said illuminating a second spray plume illuminates a side of said spray plume perpendicular to said second side.

16. A system for spray plume characterisation, comprising:
   a source of non-coherent illumination positioned for illuminating a spray plume with light such that said light impinges upon the entirety of a first side of said spray plume;
   an imaging device for imaging said illuminated spray plume from a second side perpendicular to said first side.

17. A system of characterising a spray plume, comprising:
   an actuator for operating an aerosol delivery system in a controlled manner to form a spray plume;
   a source of illumination for illuminating said spray plume with light such that said light impinges upon the entirety of a face of said spray plume;
   an imaging device positioned for imaging said spray plume from a side parallel to a spray axis of said spray plume;
   a turntable having a rotational axis parallel to said spray axis for rotating said aerosol delivery system.

18. A system of characterising a spray plume, comprising:
   means for operating an aerosol delivery system in a controlled manner to form a first spray plume and, subsequently, a second spray plume;
   means for illuminating said first spray plume with light such that said light impinges upon the entirety of a face of said first spray plume and for illuminating said second spray plume with light such that said light impinges upon the entirety of a face of said second spray plume; and
   means for imaging said first spray plume from a first side parallel to a spray axis of said spray plume and for imaging said second spray plume from a second side parallel to a spray axis of said spray plume, said second side being perpendicular to said first side.

* * * * *